United States Patent
Wilkinson et al.

(10) Patent No.: US 6,682,569 B2
(45) Date of Patent: Jan. 27, 2004

(54) PROSTHETIC APPARATUS WITH ELASTOMERIC SHOCK ABSORBER ELEMENT

(76) Inventors: Kerry E. Wilkinson, 5750 W. Linda La., Chandler, AZ (US) 85226; Randall S. Whiteside, 14018 S. 8th St., Phoenix, AZ (US) 85048

( * ) Notice: Subject to any disclaimer, the term of this patent is extended or adjusted under 35 U.S.C. 154(b) by 72 days.

(21) Appl. No.: 10/138,812

(22) Filed: May 6, 2002

(65) Prior Publication Data

US 2002/0147501 A1 Oct. 10, 2002

Related U.S. Application Data

(63) Continuation-in-part of application No. 09/828,671, filed on Apr. 9, 2001, now Pat. No. 6,468,315.

(51) Int. Cl.⁷ .................................................. A61F 2/80
(52) U.S. Cl. ..................................... 623/35; 267/140.13
(58) Field of Search .............................. 623/27, 32, 33, 623/34, 35, 36, 38, 57; 267/140.11, 140.13

(56) References Cited

U.S. PATENT DOCUMENTS

| | | | | | |
|---|---|---|---|---|---|
| 3,878,867 A | * | 4/1975 | Dirks | ........................... | 138/30 |
| 5,464,442 A | * | 11/1995 | Burt et al. | ..................... | 623/27 |
| 5,547,172 A | * | 8/1996 | Corcoran | ............... | 267/140.13 |
| 5,888,214 A | * | 3/1999 | Ochoa | .......................... | 623/27 |
| 5,961,556 A | * | 10/1999 | Thorn | .......................... | 623/27 |
| 6,214,056 B1 | * | 4/2001 | Wilkinson | .................... | 623/35 |

* cited by examiner

*Primary Examiner*—Corrine McDermott
*Assistant Examiner*—Will H Matthews
(74) *Attorney, Agent, or Firm*—H. Gordon Shields

(57) ABSTRACT

Prosthetic apparatus includes a pyramid adaptor and a pylon connected together by an outer sleeve, which may be an elastomeric element. The sleeve or element is clamped to both the pyramid adaptor and to the pylon to provide shock absorbing characteristics and to allow relative axial rotation between the pyramid adaptor and the pylon. Different configurations or embodiments of sleeves are illustrated, and the use of a third clamp is also illustrated.

5 Claims, 3 Drawing Sheets

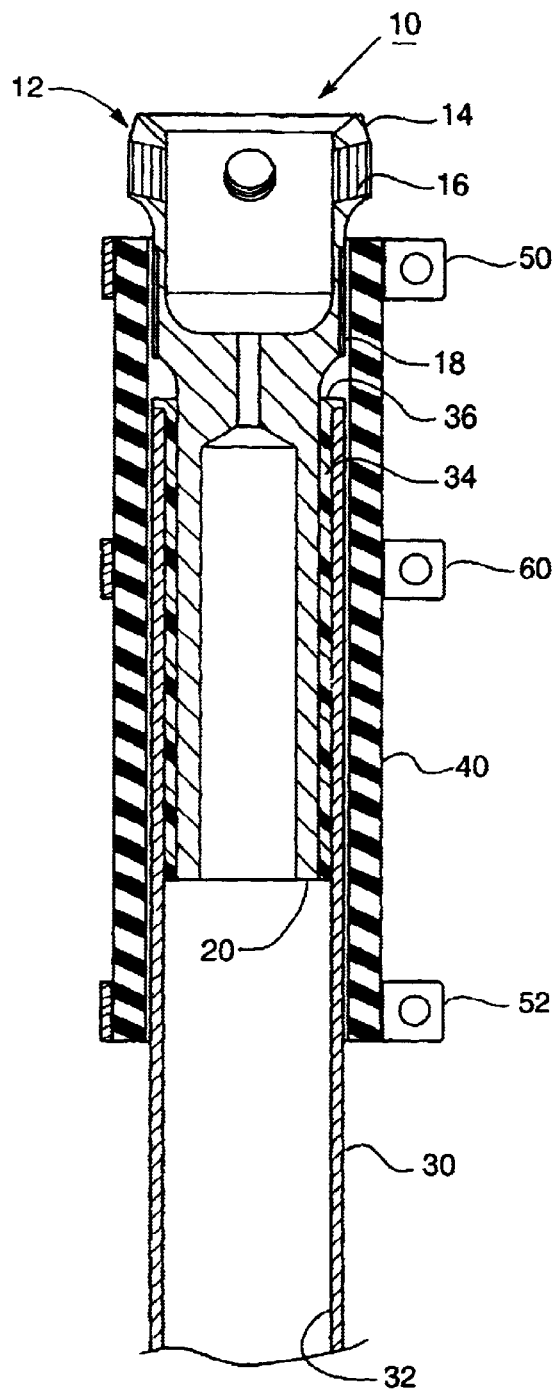
FIG. 3.
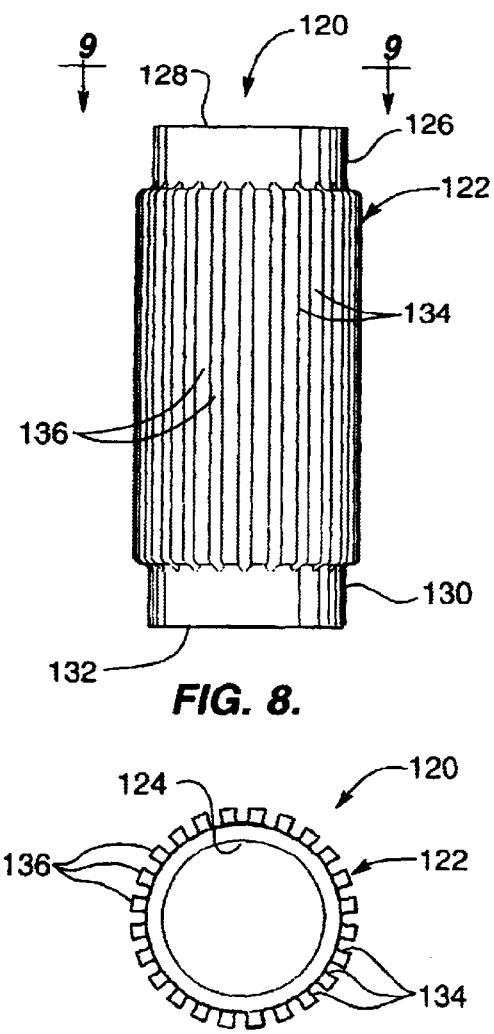
FIG. 8.
FIG. 9.

US 6,682,569 B2

PROSTHETIC APPARATUS WITH ELASTOMERIC SHOCK ABSORBER ELEMENT

CROSS REFERENCE TO RELATED APPLICATION

This application is a continuation-in-part application of Ser. No. 09/828,671, filed Apr. 9, 2001 now U.S. Pat. No. 6,468,315.

BACKGROUND OF THE INVENTION

1. Field of the Invention

This invention relates to a prosthetic apparatus, and, more particularly, to a shock absorber apparatus for a prosthetic leg for both axial shock absorption and relative torsional or rotational movement.

2. Description of the Prior Art

There are generally two problems with prosthetic leg apparatus including the inability to absorb shocks and the inability to rotate. Shock absorption increases the natural feel and comfort of the leg, and the rotation of varying degrees allows a more ordinary turn while walking, or allows a combination of pivoting action required for sports activities of different types.

An effort to overcome the problems is shown in U.S. Pat. No. 5,800,562, dated Sep. 1, 1998, the inventor of which is co-inventor herein. The '562 patent utilizes elastomeric elements and a spring element to provide both vertical and torsional movement. The elastomeric elements provide vertical shock absorber action and, with the spring element, also allow a degree of rotational movement and shock absorber action.

Another example of the prior art is found in co-pending application, Ser. No. 09/389,735, filed Sep. 7, 1999, the inventor of which is co-inventor herein. The '562 patent may be considered as the first generation apparatus, while the '735 application may be considered the second generation apparatus, with the present invention as the third generation, each of which utilizes an elastomeric element for shock absorbing capabilities and, with other elements, for torsion relative rotation or movement as well. However, the present apparatus utilizes an elastomeric element for both shock absorbency and torsional resistance or movement, without the need for other elements.

SUMMARY OF THE INVENTION

The invention described and claimed herein comprises a shock absorber for a prosthetic leg utilizing an elastomeric element which also offers torsional resistance to allow the user of the prosthetic apparatus to rotate, thus simulating the natural movement of a leg and ankle. The elastomeric element is secured between a lower pylon element and an upper pyramid adaptor element and is disposed on the outside of both elements. The elastomeric element is the only fixed connection between the pylon and the pyramid adaptor. The extent of the cushioning or shock absorbency and the extent of the torsional resistance may be varied by different types of elastomeric elements and by the location on the pylon on which the elastomeric element is secured.

Among the objects of the present invention are the following:

To provide new and useful shock absorber apparatus for a prosthetic leg;

To provide new and useful prosthetic leg apparatus having both longitudinal or axial shock absorber characteristics and rotational pivoting characteristics;

To provide an elastomeric element disposed outside of a pylon and secured to a pylon and a pyramid adaptor;

To provide an elastomeric element having a plurality of vertically extending grooves disposed outside of a pylon and secured to a pylon and a pyramid adapter;

To provide new and useful prosthetic apparatus for absorbing axial shocks and for permitting twisting or torsional relative movement;

To provide new and useful prosthetic apparatus including a pyramid adaptor and a pylon secured together by an elastomeric element; and To provide new and useful elastomeric elements usable in a prosthetic apparatus and having different torsional and longitudinal shock absorbing characteristics.

BRIEF DESCRIPTION OF THE DRAWING

FIG. 3 is a view in partial section of the apparatus of FIG. 1.

FIG. 8 is a front view of another alternate embodiment of the present invention.

FIG. 9 is a top view of the apparatus of FIG. 8, taken generally along line 9—9 of FIG. 8.

DESCRIPTION OF THE PREFERRED EMBODIMENT

Figure 1:
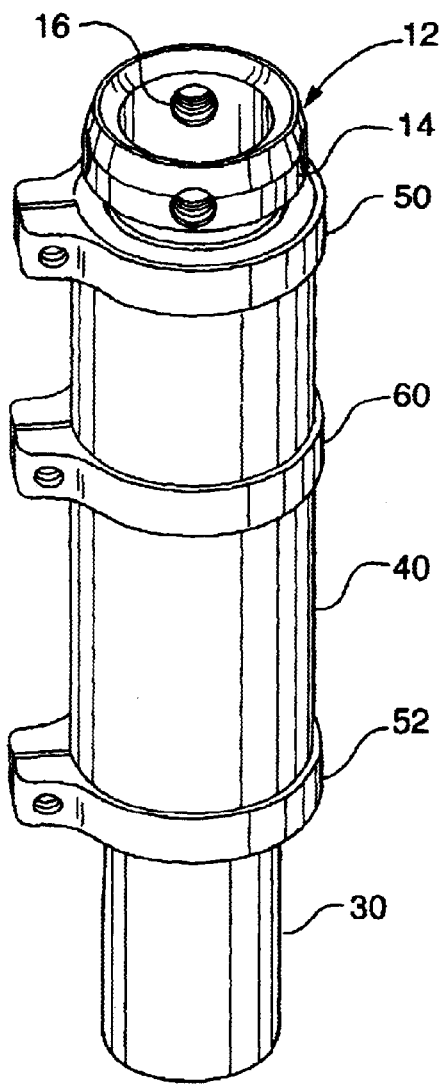
FIG. 1 is a perspective view of the apparatus of the present invention.
Figure 2:
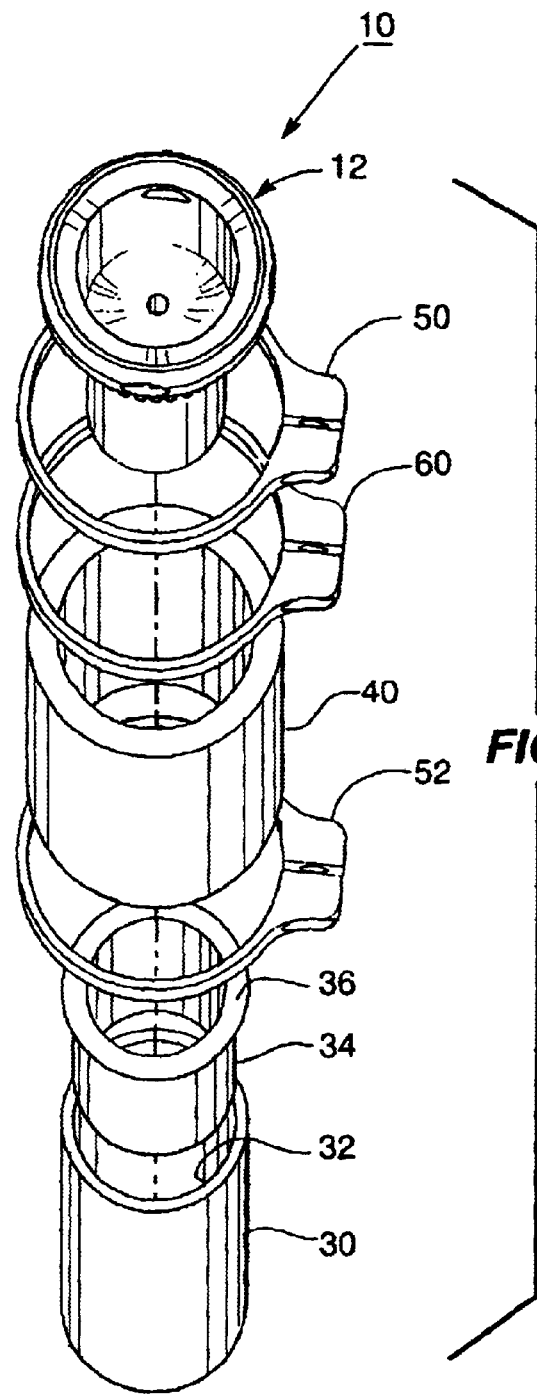
FIG. 2 is an exploded perspective view of the apparatus of FIG. 1.

FIG. 1 is a perspective view of prosthetic shock absorber apparatus 10 of the present invention. FIG. 2 is an exploded perspective view of the shock absorber apparatus 10 of FIG. 1. FIG. 3 is a view in partial section of the shock absorber apparatus 10. For the following discussion, reference will be made to FIGS. 1, 2, and 3.

The prosthetic shock absorber apparatus 10 includes a pyramid adaptor 12 movable relative to a pylon 30. The pyramid adaptor 12 includes an upper portion 14 and four spaced apart screw bores 16, well known and understood in the industry. The screw bores 16 are disposed at the top or upper portion 14 of the pyramid adaptor 12. Extending downwardly from the upper portion 14 is a generally circular clamp land 18. Below the clamp land 18 is a lower cylindrical portion 20. The cylindrical portion 20 is relatively long, as compared to the upper portion 14 where the screw bores 16 and the clamp land 18 are located.

The cylindrical portion 20 has a diameter which is slightly less than the diameter of the clamp land 18. The outer diameter of the lower cylindrical portion 20 is less than the outer diameter of the clamp land 18, and the outer diameter of the clamp land 18 is less than the diameter of the upper portion 14 of the pyramid adaptor 12 where the screw bores 116 are disposed.

The cylindrical portion 20 of the pyramid adaptor 12 extends into a bore 32 of the pylon 30. Relative movement between the pylon 30 and the cylindrical portion 20 is enhanced by a bushing 34. The bushing 34 is disposed on the inner bore portion 32 of the pylon 30. The pylon 30 is a tubular cylindrical member, and the lower cylindrical portion 20 extends into the bushing 34 in the bore 32 of the pylon 30. The bushing 32 is appropriately secured to the upper portion of the pylon 30, with a top 36 of the bushing 34 disposed on the top of the pylon 30.

The cylindrical portion 20 moves in the bushing 34 and in the bore 32 of the pylon in accordance with the movement of the user of the prosthetic apparatus 10. The relative movement between the two elements 12 and 30 is limited both axially and rotationally by an elastomeric sleeve or element 40, as discussed below.

While the length of the bushing 34 is shown in FIG. 3 as coinciding with the length of the cylindrical portion 18, this is merely illustrative. As will be understood, relative movement between the cylindrical portion 18 and the pylon 30 would, of necessity, render a different visual effect from that illustrated in FIG. 3.

Disposed on the outside of both the pylon 30 and the pyramid adaptor 12 is the elastomeric element 40. The elastomeric element 40 provides the shock absorbing characteristics and also allows a twisting or torsional relative movement between the pyramid adaptor 12 and the pylon 30. As is well known and understood, the pylon 30 extends to a prosthetic foot appliance. Such prosthetic foot appliance is, of course, not illustrated in the present drawing.

The elastomeric element 40 is secured to the clamp land 18 of the pyramid adaptor 12 by an appropriate upper clamp 50. The elastomeric element 40 is secured to the pylon 30 by a lower clamp 52. Thus, the elastomeric element is the only element connecting the pyramid adaptor 12 and the pylon 30.

The extent to which the elastomeric element 40 absorbs shocks and permits twisting or torsional relative movements depends on several factors, including a stiffness or resilience of the element 40 and the inherent characteristics of the element 40, which may be varied according to the thickness of the elastomeric element, the composition of the elastomeric element, and various design factors of the elastomeric element, as will be discussed below in conjunction with FIGS. 4, 5, 6, and 7.

In addition to the design or characteristics of the elastomeric element 40 itself, a third clamp may be used to also vary both the shock absorbing characteristics and the torsional characteristics of the elastomeric element 40 by the location of such third clamp relative to the pylon 30. This is illustrated by an intermediate clamp 60, and its placement. The clamp 60 is illustrated in FIGS. 1, 2, and 3. The higher the clamp 60 is located on the pylon 30, or the closer to the upper portion of the pylon 30, the less the shock absorbing characteristics of a given elastomeric element, and the more limited the torsional capability of the elastomeric element will be. Obviously, such third clamp may or may not be advantageous, depending on the various characteristics as discussed above, and this will be discussed in detail below, of a given elastomeric element.

Figure 4:
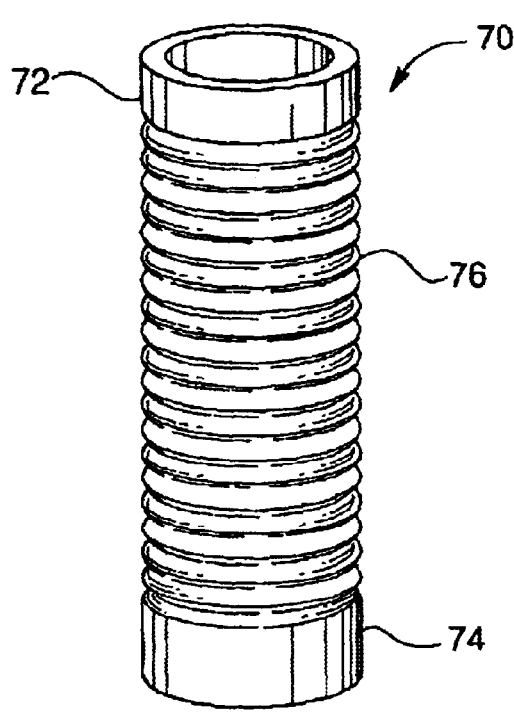
FIGS. 4, 5, and 6 are perspective views of alternate embodiments of a portion of the apparatus of FIGS. 1, 2, and 3.

Various configurations of elastomeric elements are illustrated in FIGS. 4, 5, 6, and 7, which comprise perspective views of elastomeric elements. In FIG. 4, an elastomeric element 70 is shown. The element 70 includes a smooth upper portion 72 and a smooth lower portion 74. The smooth portion 72 and 74 are, respectively, the upper portion and lower portion which receive clamps for clamping the element 70 to, respectively, the pyramid adaptor 12 and the pylon 30.

Between the smooth portion 72 and 74 is an intermediate portion 76 which comprises a plurality of circular ribs 76. The relative length of height of the ribs, and the extent of their thickness and the relative thickness of the element between the ribs, or the indentations between adjacent ribs, will vary the characteristics, for both the shock absorbing characteristics and the torsional characteristics of the element 70.

Figure 5:
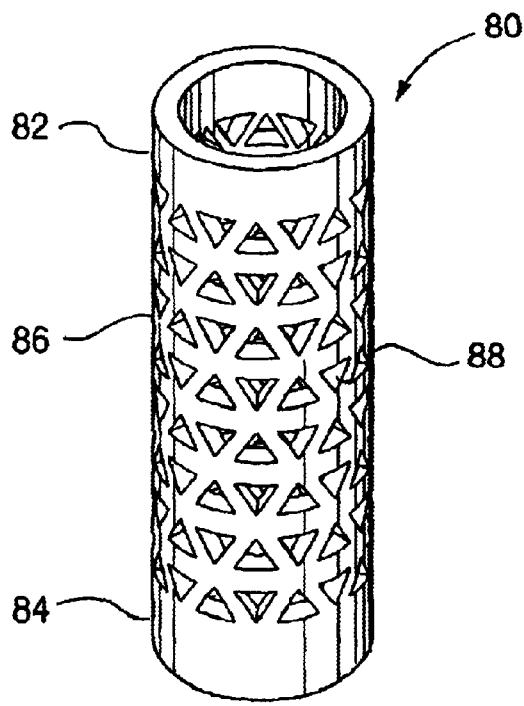

A different type of shock absorber element is shown in FIG. 5, in which a shock absorber element 80 is shown in perspective. The shock absorber element 80 includes a smooth upper portion 82 and a smooth lower portion 84. The portions 82 and 84 are, of course, the clamping locations for securing the element 80 to the pyramid adaptor 12 and to the pylon 30. Between the two smooth portions 82 and 84 is an intermediate portion 86 through which extends a plurality of triangularly configured apertures. The triangular apertures are shown in alternate "up" and "down" arrangements. The use of such apertures is, of course, to vary the shock absorber and rotational characteristics of the element 80. The size of the apertures may vary, and the spacing between apertures and between rows of apertures, may also vary, depending on the characteristics desired of the element.

Figure 6:
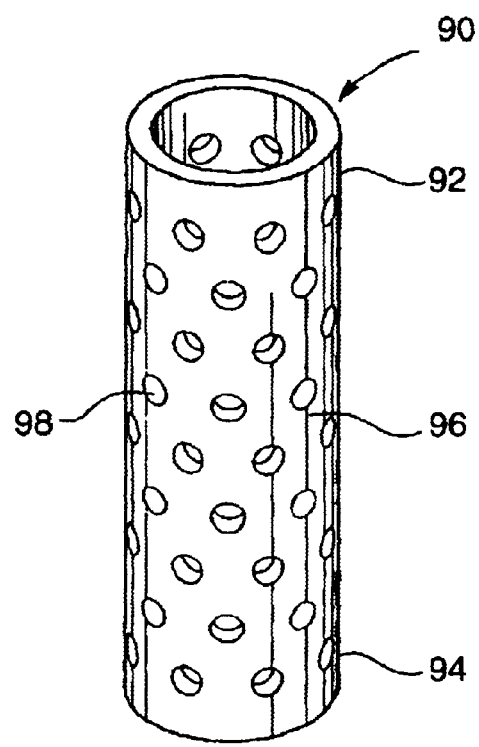

FIG. 6 is a perspective view of another shock absorber element 90. The element 90, like the elements 70 and 80, includes a smooth upper surface and a smooth lower surface indicated, respectively, by reference numerals 92 and 94, and an intermediate portion 96 between the two smooth portions. The intermediate portion 96 has a plurality of circular apertures 98 extending through. The size of the apertures 98 and their particular orientation, may vary, again as desired to provide a desired shock absorbing and rotational or torsional characteristics of the element 90.

Figure 7:
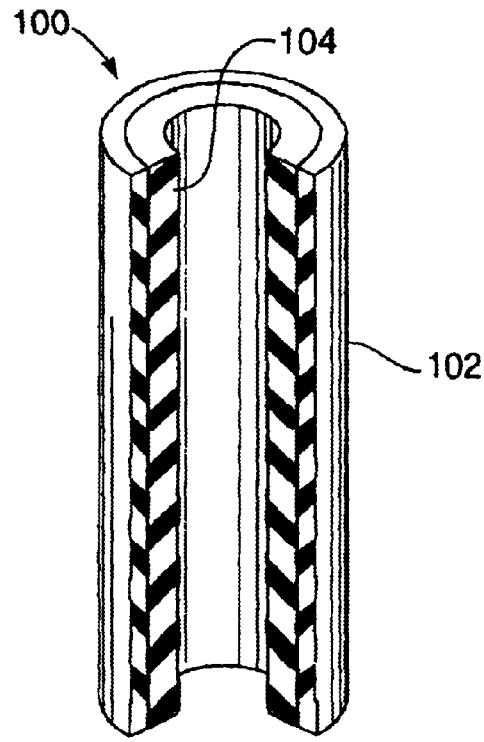
FIG. 7 is a perspective view of another alternate embodiment, partially cut away, of a portion of the apparatus of FIGS. 1, 2, and 3.

FIG. 7 discloses a double element 100 which includes an outer element 102 and an inner element 104. The elements 102 and 104 are different in thickness and may be different in composition to provide the desired shock absorber and twisting or torsional characteristics of the element 100.

The elements 40, 70, 80, 90, and 100 are essentially sleeves which connect the pyramid adaptor 12 to the pylon 30. Their particular design characteristics, as illustrated in the drawing figures, and which may be of other different configurations, are designed to provide specific shock absorber and torsional characteristics for a particular apparatus, or a particular user, or the user's desired activities. These characteristics, obviously, may vary depending on the size of the person to whom the apparatus 10 will be secured, to a particular situation, and the like.

For example, if the apparatus 10 is to be used for merely walking, one particular sleeve element 40 may be used, while a different type of sleeve or element may be used if the apparatus 10 is to be used for running, playing golf, or some other activity. Indeed, an individual may have several sleeves or elements which may be interchanged with the same pyramid adaptor and pylon, depending on the desired activities of the user. Also, as discussed above, the use of a third clamp, disposed between the two clamps which secure the elastomeric sleeve element to the respective pyramid adapter and the pylon, may also be used to vary the characteristics of any particular sleeve element by varying the location of the third clamp on the sleeve and the pylon.

FIG. 8 is a front view of a sleeve 120, which comprises another alternate embodiment of an elastomeric element of the apparatus of the present invention. FIG. 9 is a top view of the apparatus 120, taken generally along line 9—9 of FIG. 8. For the following discussion, reference will be made to FIGS. 8 and 9.

The sleeve 120 is an elastomeric element having a generally cylindrical configuration, like the other elastomeric elements discussed above. The sleeve 120 comprises an elastomeric cylinder 122 which has an inner bore 124. The bore 124 receives the mating portions of the clamp land 18 and the pylon 30, as may be understood from FIG. 3. The cylinder 122 includes a top surface 128 adjacent to a top clamp portion 126. At the lower portion of the cylinder 122 is a bottom clamp portion 130. The bottom clamp portion 130 is adjacent to a bottom surface 132.

Extending between the top and bottom clamp portions 126 and 130 are a plurality of vertically axially extending grooves 134. Between the grooves are a plurality of axially extending ribs or lands 136. The grooves 134 are generally aligned with the top and bottom clamp portions 126 and 130. That is, the outer diameter of the cylinder 122 at the clamp portions 126 and 130 is generally the same as the diameter of the cylinder 122 at the grooves 134. Accordingly, the diameter of the cylinder 122 through the ribs or lands 136 is greater than the diameter of the cylinder 122 at the clamp portions and at the grooves. This is best shown in FIG. 9.

The purpose of providing the greater diameter of the cylinder through the ribs or lands 136, with adjacent grooves 134, is to provide a stiffening of the elastomeric element to provide more vertical or axial shock resistance without sacrificing any torsional or rotational capability, as compared to the previously discussed embodiments. The vertical ribs 136 and the grooves 134 provide such capability.

The different embodiments provide specialized shock absorbing and torsional movement characteristics for different purposes. As discussed above, the apparatus 120 provides somewhat greater vertical shock absorbing characteristics while minimizing additional rotational resistance, as compared to the previously discussed embodiments. The number of lands and grooves, and the extent or increased diameter of the lands, as compared to the diameter of the groove portion of the apparatus, may vary according to the size or weight of the user of the apparatus and according to the specific use which the user may desire. Specific elements or apparatus for an individual may vary depending upon the specific use or purpose desired by the user. Thus, a user may desire one size for ordinary walking and others for athletic uses, and the like.

Moreover, the composition of the elastomeric material out of which the sleeves are made may vary according to the same general parameters as discussed in the next previous paragraph, namely the size of the user and the purpose of the sleeve. Thus, for any individual user, elastomeric sleeves may vary in configuration and composition. Since the sleeves are easily and quickly changed, a user may have a number of sleeves, each with different characteristics to be used different purposes or different specific uses.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, within the limits only of the true spirit and scope of the invention.

What we claim is:

1. Prosthetic shock absorber apparatus comprising in combination:

a cylindrical element;

a pylon movable relative to the cylindrical element;

an elastomeric element, having a plurality of vertically extending grooves, disposed about the cylindrical element and the pylon;

a first clamp for securing the elastomeric element to the cylindrical element; and a second clamp for securing the elastomeric element to the pylon, whereby the elastomeric element absorbs axial shocks and permit torsional relative rotation as the pylon and the cylindrical element move relative to each other.

2. The apparatus of claim 1 which further includes a top clamp portion on the elastomeric element, and the first clamp is disposed on the elastomeric element at the top clamp portion.

3. The apparatus of claim 2 which further includes a bottom clamp portion on the elastomeric element, and the second clamp is disposed on the elastomeric element at the bottom clamp portion.

4. The apparatus of claim 3 which includes a plurality of vertically extending lands between the plurality of vertically extending grooves.

5. The apparatus of claim 4 in which the plurality of grooves are aligned with the top and bottom clamp portions.

* * * * *